(12) United States Patent
Krueger (10) Patent No.: US 7,527,247 B1
(45) Date of Patent: May 5, 2009

(54) APPARATUS AND METHOD FOR EXPOSING AIR TO AN AROMATIC SUBSTANCE

(76) Inventor: Robert Curtis Krueger, 2064 W. Ave. - J Suite 385, Lancaster, CA (US) 93536

(*) Notice: Subject to any disclaimer, the term of this patent is extended or adjusted under 35 U.S.C. 154(b) by 348 days.

(21) Appl. No.: 11/242,470

(22) Filed: Oct. 3, 2005

(51) Int. Cl.
*B01F 3/04* (2006.01)

(52) U.S. Cl. .................. 261/29; 261/88; 261/DIG. 88

(58) Field of Classification Search ............ 261/28, 261/29, 84, 88, DIG. 88
See application file for complete search history.

(56) References Cited

U.S. PATENT DOCUMENTS

| | | | | |
|---|---|---|---|---|
| 1,190,386 A | * | 7/1916 | Dickerson | 96/284 |
| 1,626,667 A | * | 5/1927 | Cramer et al. | 261/91 |
| 2,267,835 A | * | 12/1941 | Norris | 261/28 |
| 2,537,833 A | * | 1/1951 | Joos | 261/28 |
| 2,874,797 A | * | 2/1959 | Flury | 96/239 |
| 3,110,748 A | * | 11/1963 | Myklebust | 261/29 |
| 3,151,188 A | * | 9/1964 | Weatherston et al. | 261/29 |
| 3,220,707 A | * | 11/1965 | Weatherston et al. | 261/22 |
| 3,283,478 A | * | 11/1966 | Katzman et al. | 96/284 |
| 3,290,021 A | * | 12/1966 | Blachly et al. | 261/29 |
| 3,294,376 A | * | 12/1966 | Eranosian | 261/29 |
| 3,348,821 A | * | 10/1967 | Martin et al. | 261/29 |
| 3,376,025 A | * | 4/1968 | Flury | 261/29 |
| 3,528,781 A | * | 9/1970 | Gelfman et al. | 422/169 |
| 3,914,349 A | * | 10/1975 | Stipanuk | 261/29 |
| 5,147,581 A | * | 9/1992 | Lu | 261/24 |
| 6,131,889 A | * | 10/2000 | Birdsell et al. | 261/29 |

* cited by examiner

*Primary Examiner*—Scott Bushey (57) ABSTRACT

An apparatus for exposing air to an aromatic substance (26) at a uniform level of aroma for a certain period of time without using gas, fire, or applied electric heat source. The invention has an aromatic solution tank (31) on which sits a lid (30) under which is mounted a motor (32) engaged by a microswitch (34). Disposed on the motor shaft is an impeller (36) generating a guide air flow through a chamber of free space in the tank via an intake housing (35), inlet (21*a*) and outlet (25*b*) holes in the lid, and attached a draw tube (37). Rotation (20) of the draw tube delivers a 360 degree sheet of aromatic solution (24) across flowing air (22), air which is then discharged (25*a*) to environment. Consequently, air flowing through the swirl of aromatic solution is exposed at a uniform level for a certain period of time.

12 Claims, 7 Drawing Sheets

Transparent Side View of the apparatus and the method.

FIGURE 1

Figure 1:
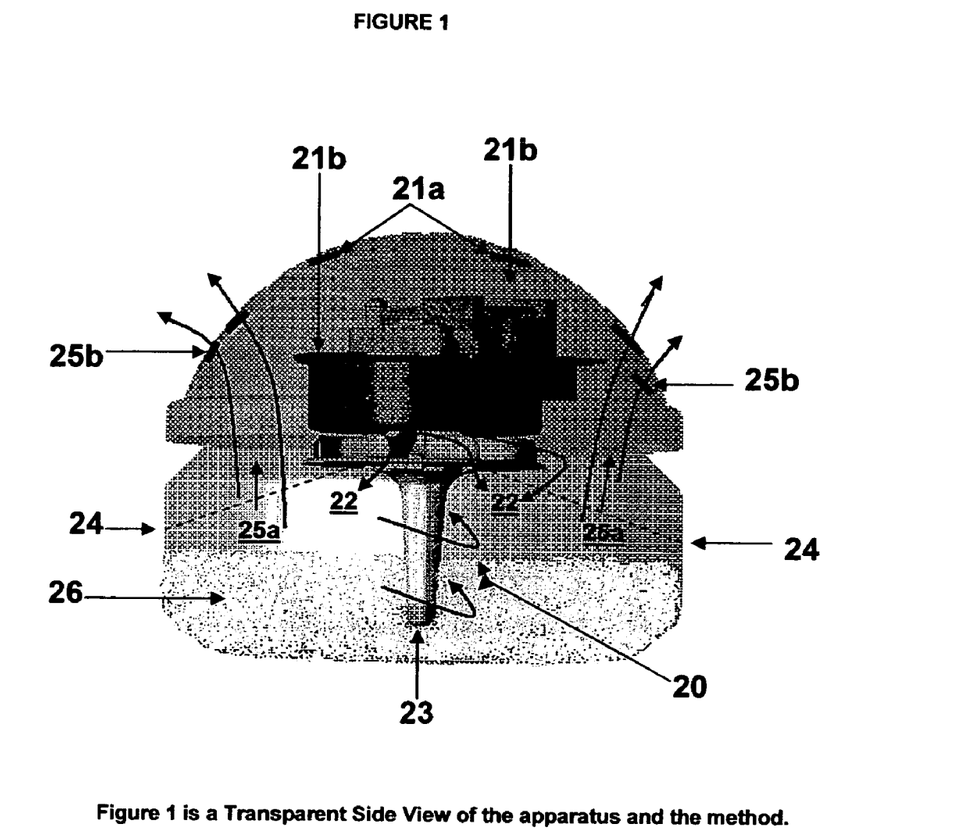

Figure 1 is a Transparent Side View of the apparatus and the method.

FIGURE 2A

Figure 2A:
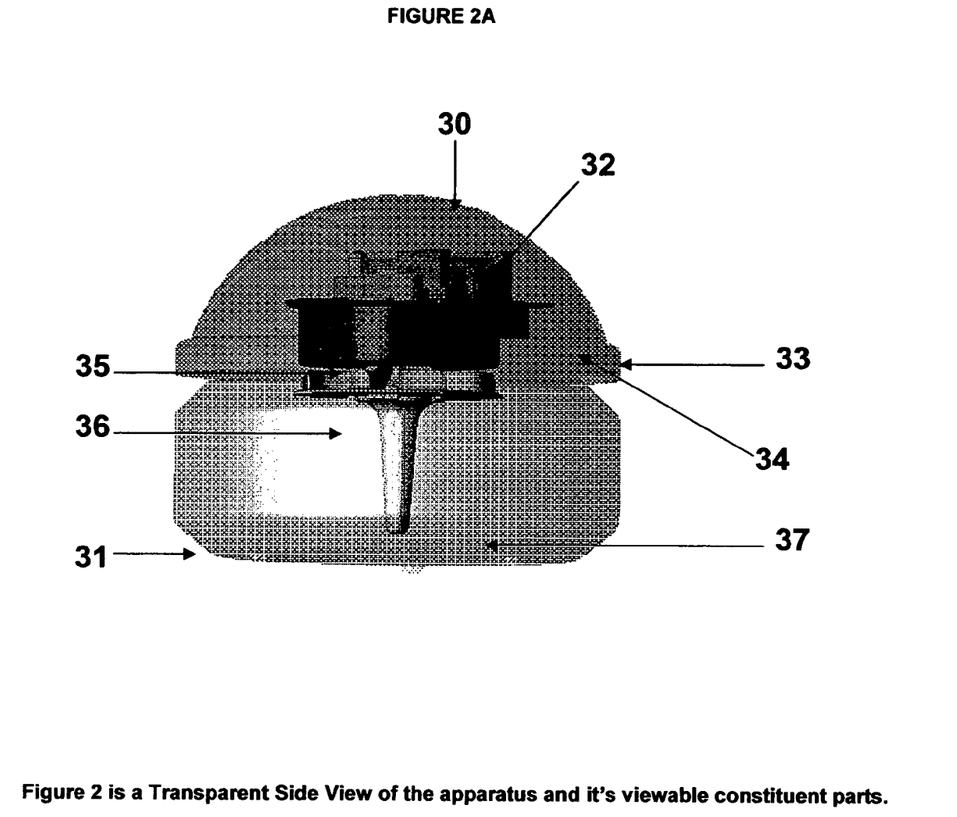

Figure 2 is a Transparent Side View of the apparatus and it's viewable constituent parts.

FIGURE 2B

Figure 2B:
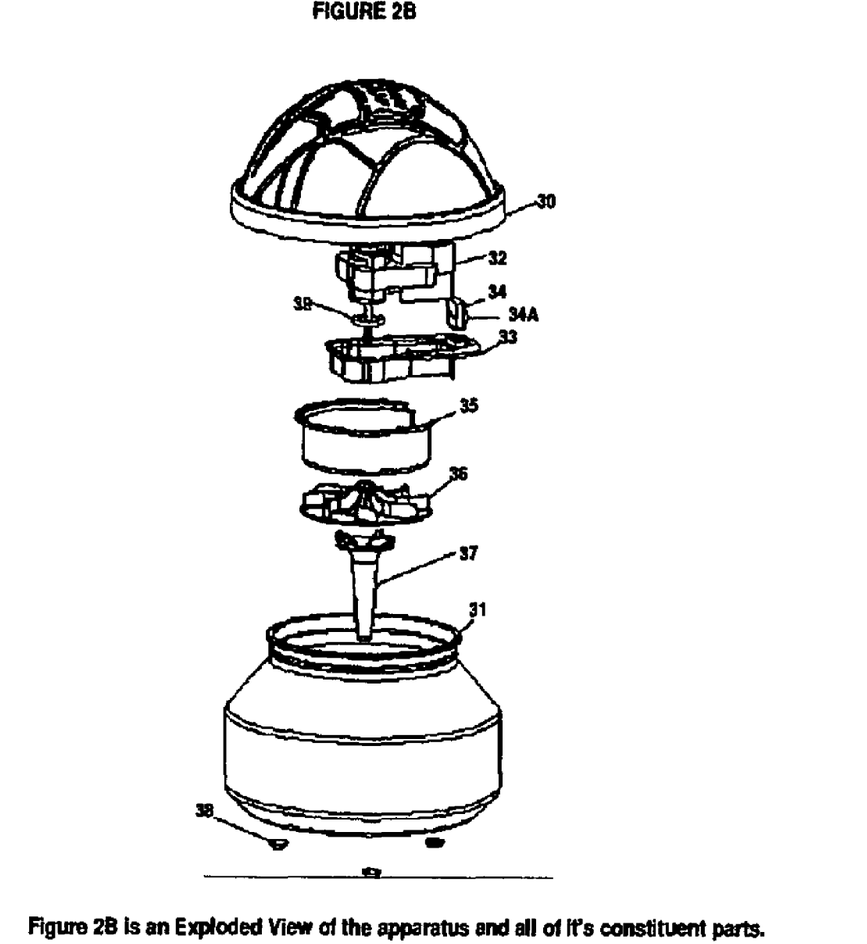

Figure 2B is an Exploded View of the apparatus and all of it's constituent parts.

FIGURE 3A

FIGURE 3B

Figure 3A:
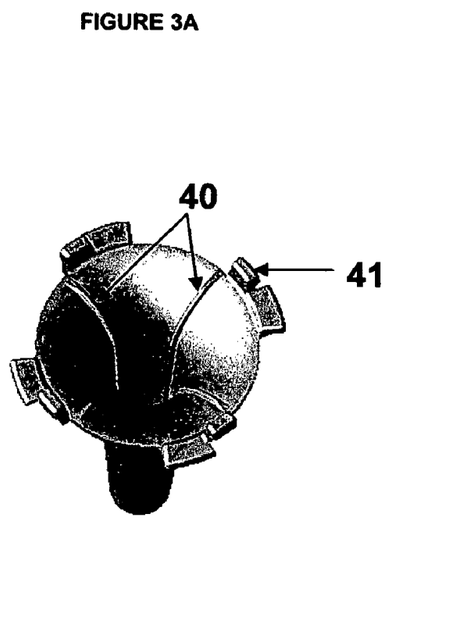
Figure 3B:
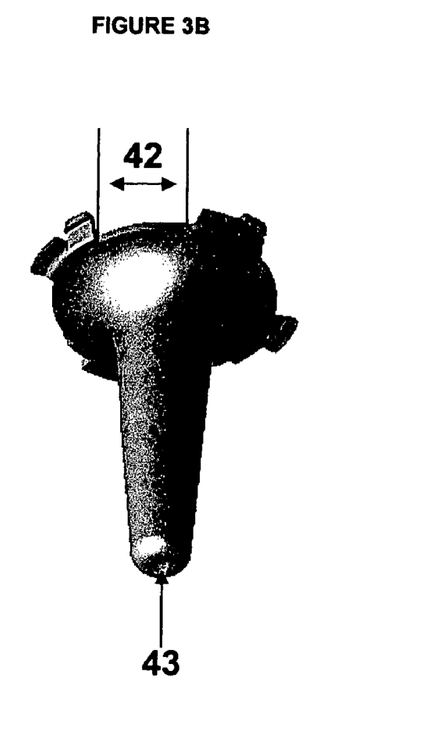

Figure 3A and 3B are Perspective Views of the draw tube.

FIGURE 4A

FIGURE 4B

Figure 4A:
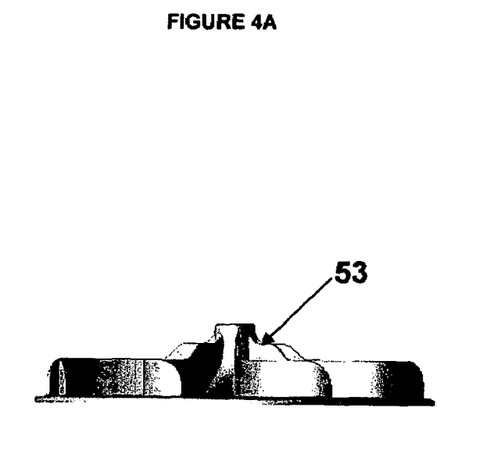
Figure 4B:
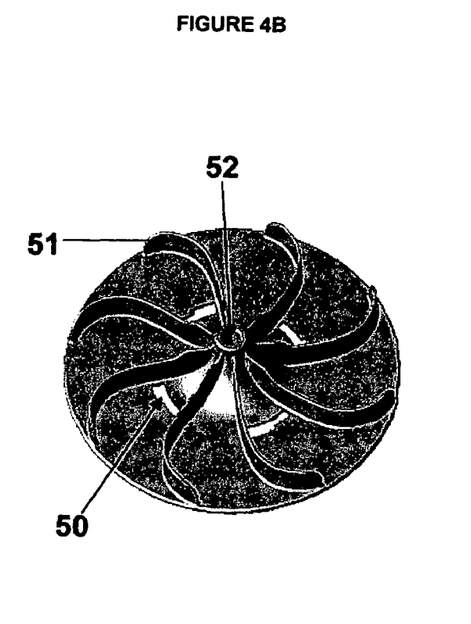

Figure 4A and 4B are a Side View, and a Top Perspective View of the impeller.

FIGURE 5A

FIGURE 5B

Figure 5A:
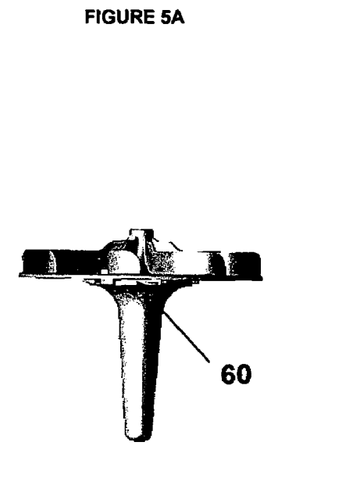
Figure 5B:
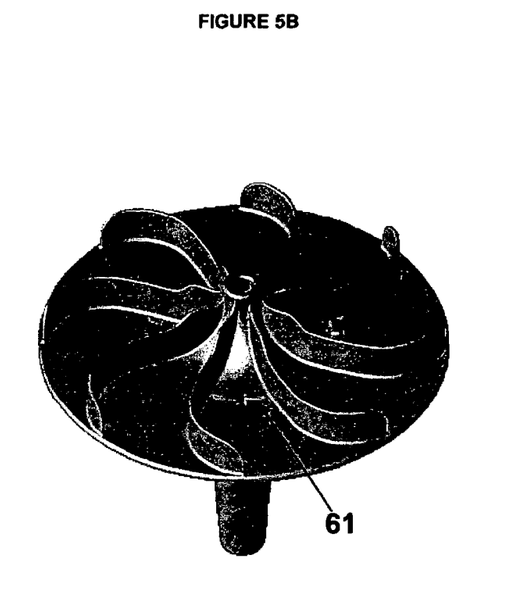

Figure 5A and 5B are a Side View, and a Top Perspective View of the draw tube – impeller assembly.

Figure 6

Figure 6:
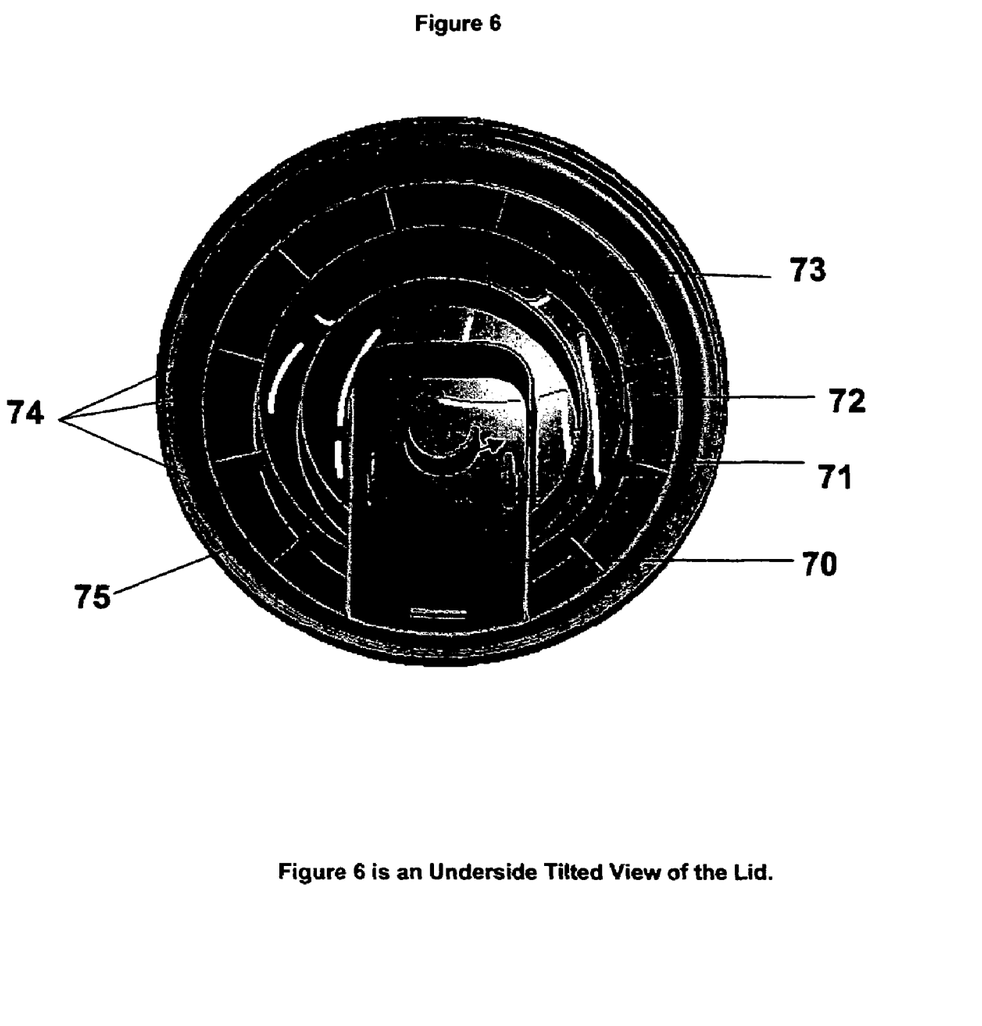

Figure 6 is an Underside Tilted View of the Lid.

APPARATUS AND METHOD FOR EXPOSING AIR TO AN AROMATIC SUBSTANCE

BACKGROUND OF THE INVENTION

An apparatus for exposing air to an aromatic substance at a uniform level of aroma for a certain period of time without the use of a gas, fire, or applied electric heat source. The apparatus comprises a housing embodied as an upper lid part, and a lower reservoir tank part. The upper lid part includes at least one air inlet hole and at least one air outlet hole that permits air to be sucked into the closed free space mixing chamber wherein the air comes into contact with a liquid aromatic substance spray, and then wherein said air is exhausted to the environment at a uniform rate. The apparatus also includes an impeller means, driven by a motor, for generating an air flow through the free space mixing chamber, and a pump means for producing a liquid flow within the chamber.

DESCRIPTION OF THE RELATED ART

Aromatics today find widespread use, ranging from deodorizing purposes in restrooms, to the aromatizing of homes, offices, and businesses. The popularity is, at least partially, motivated by the increase of foul odors in urban areas, as well as the greater appreciation of the positive health effects of aromatherapy. Conventional dynamic aromatic emission devices spray in aerosols an aromatic substance contained in a vessel of the device, utilize heat on an aromatic substance to evaporate it, or utilize a directly applied electrical means to dissipate the aromatic substance. Conventional static aromatic emission devices rely upon the natural chemical breakdown process of an aromatic substance that has been layered onto a static object, such as cardboard, to dissipate the aroma.

Although various devices are used to convey an aromatic substance into the environment, they are generally not suitable to safely deliver a particular aroma at a uniform level over a known period of time. Often, these devices will produce a strong aroma initially, but the intensity of the aroma quickly fades. In addition, many of these known devices produce safety hazards such as aerosol gases, fire, smoke, and electric shock, making them generally not suitable for domestic use. Lastly, many of the devices used today to convey an aromatic substance into the environment are small enough to be placed into a child's mouth, rendering them a choking hazard.

Prior art designed specifically to clean, filter, or humidify the air using water, as opposed to this invention that comprises a means to specifically subject air to an aromatic substance, employ a "rotary pump" structure that appears outwardly as functionally the same to the "draw tube" comprised in this invention, but that comprise differences that could not be considered "obvious" in nature. One such apparatus having a rotary pump structure is known as U.S. Pat. No. 4,749,389—Worwag dated Jun. 7, 1988 and corresponding to a method and apparatus for humidifying and purifying the air of a room. The draw tube of this current invention has 'ribs' extending downward and axially inside the conical shape, while the rotor tube of the Worwag apparatus does not. These ribs serve to improve and stabilize the pumping action of the aromatic liquid, and increases the flow rate substantially. As the draw tube turns, the aromatic liquid runs up these ribs to the top of the draw tube in a more stable fashion. To a degree, the greater the height of the ribs, the greater the flow rate. Additionally, the conical shape of the draw tube of this invention extends upwardly and axially directly to the outlet channels. It does not extend upward and axially past the outlet channels and then back down like the rotor tube of the Worwag apparatus. The draw tube of this invention has a better direct path to the outlet, and thus is more efficient.

In other prior art, an apparatus designated specifically as an air cleaner comprising a "water pipe" and a "screw" inside the pipe is known as WO01/89664 [Kwon]—Nov. 29, 2001, a Korean patent designating the United States in an international application. When the Kwon water pipe is rotated by a motor, the screw which is installed inside the water pipe lifts the water from a reservoir and is sprayed horizontally through lots of small holes of the injection pipe located at the top. The Kwon "screw" mechanism to draw water up from the reservoir is essentially an archimedies screw which differs greatly in overall structure from the draw tube comprised in this invention, and due to internal friction is prone to wear and mechanical failure. Unlike the Kwon apparatus, the draw tube of the current invention is not comprised of interrelated moving parts, therefore is less prone to repair downtime, and the operational lifespan of the apparatus is enhanced.

The current invention is a novel apparatus designed for exposing air to an aromatic substance, and is not an apparatus to humidify, purify, or filter the air.

SUMMARY OF THE INVENTION

Accordingly, it is an object of the present invention is to provide a new and improved apparatus for exposing air to an aromatic substance that will overcome some of the difficulties in the prior art, or at least, provide the public with a viable alternative for domestic use. It is another object of the present invention to provide an apparatus for exposing air to an aromatic substance at a uniform level for a fixed period of time without the use of gas, fire, or a directly applied electric heat source. It is yet another object of the present invention to provide an apparatus for exposing air to an aromatic substance in a safe, efficient and reliable manner.

To achieve the above objects, the present invention comprises a housing embodied as an upper lid part, and a lower reservoir tank part. The upper lid part comprises at least one air inlet hole and at least one air outlet hole, and an impeller attached to a motor to facilitate the movement of air though the apparatus. The upper lid part also comprises a draw tube attached to the underside of the impeller, and that when rotated acts as a pump means to provide a liquid flow within the free space mixing chamber.

During operation, the liquid, preferably an aromatic substance soluble in water and mixed therein, is conveyed upward by the rotation of the draw tube wherein the liquid is forcefully discharged 360 degree's horizontally and downwardly through the wide and narrow outlet channels that are disposed in a radial manner about the axis of the draw tube. The liquid then flows into the free space mixing chamber created between the surface of the liquid in the reservoir tank, and the underside of the upper lid part. When the air flow comes into contact with the spraying aromatic liquid, the air flow is spun into a plurality of smaller flows, and an intensive mutual mixing of air and aromatic liquid substance takes place. At the same time, the mixing air is being pushed through the free space mixing chamber by new air constantly being drawn into the apparatus by the impeller. The mixed aromatized air is then discharged back into the environment through the small outlet hole(s) in the upper lid part. The liquid reservoir is advantageously arranged as the base of the housing so sprayed liquid can run down the sides of the housing and return to the reservoir by gravity.

To achieve a uniform level of exposure of air to an aromatic substance over a certain period of time, the motor rotates the impeller at a set constant rate, the air inlet and air outlet hole(s) in the upper lid are relatively small in area so as to reduce the amount of air flowing through the apparatus at any given moment, providing enhanced directional air guidance, and reduced air moisture content as the aroma laden air exits the apparatus back into the environment. Most known dynamic air humidifying and filtering devices utilize far larger air inlet and outlet holes acting to open a larger surface area to increase the quantity and speed of airflow through the device, often additionally comprising a physical filter (i.e. heppa filter, wet mat, granule substance), and contain one or two high speed fans to move the heavily humidified and/or filtered air out of the device.

BRIEF DESCRIPTION OF THE DRAWINGS AND PICTURES

FIG. 1 is a transparent side view of the apparatus and the method.

FIG. 2A is a transparent side view of the apparatus and its viewable constituent parts.

FIG. 2B is an exploded view of the apparatus and all of its constituent parts.

FIGS. 3A and 3B are perspective views of the draw tube.

FIGS. 4A and 4B are a side view, and a top perspective view of the impeller.

FIGS. 5A and 5B are a side view, and a top perspective view of the draw tube-impeller assembly.

FIG. 6 is an underside tilted view of the lid.

DETAILED DESCRIPTION OF THE PREFERRED EMBODIMENTS

Referring now to the drawing, the embodiments of the present invention are now discussed.

The invention seeks to expose air to an aromatic substance, the apparatus embodied as a housing comprising an upper lid part (30), and a lower reservoir tank part (31). The upper lid part has at least one air inlet hole (21*a*), and at least one air outlet hole (25*b*). The underside of the upper lid part is molded to comprise a motor housing (70), an air intake chamber (71), an air outlet chamber (72), a vertical rib (73) that seals around the edge of the reservoir tank lip (80), horizontal ribs (74) that flatly position the lid atop the reservoir tank lip, and a motor heat ventilation outlet (75).

Attached to the underside of the upper lid part is a motor (32) that is engaged or disengaged by a micro-switch (34) held in place by a micro-switch retainer (34*a*). A neoprene washer (39) sits atop the face of the motor closely around the motor spindle, providing a level of protection from splashing liquid and air flow when the motor cover (33) is placed over the motor. The motor cover is tightly bonded onto the underside of the upper lid part to reduce tampering of electrical components. The air intake housing (35) sits below the air intake hole(s) (21*a*) and around the molded air intake chamber to direct inducted air, while sitting firmly atop the motor cover, providing a vacuum means for the impeller (36). The air intake housing is also tightly bonded to the underside of the lid to further prevent access and tampering of internal components. The spindle of the motor protrudes through the motor cover and the air intake housing wherein the end of said spindle is pressed into a retaining hole in the center of said impeller (52). The curvilinear nature of the impeller ribs (53) allows for the impeller to rest partially inside the air intake housing wherein a vacuum is created and air inducted, and partially outside the air intake housing wherein a fan-like (51) curvilinear rib structure facilitates the moving of inducted air through the housing.

The draw tube (37) has a liquid inlet hole (43) at its most narrow end, and internally comprises ribs (40) that extend downward and axially inside the conical shape that substantially improves the stability of the pumping action and increases the liquid flow rate. The draw tube is firmly attached to the underside of the impeller by an interlocking mechanism formed by upward protruding slide locks (41) that slide into formed holes at the base of the impeller (50), wherein a locking of the two pieces takes place (61). At such time as the draw tube and impeller are firmly attached they are referred to as the 'impeller assembly', where wide and narrow outlet channels are formed (60) axially between the two pieces whereby the liquid substance pumped up to the top of the draw tube when rotated is allowed to exit as a dispersing spray. The outlet channels formed are wide (42) so as to produce a wide angle of liquid dispersion, yet narrow to generate smaller liquid droplets thereby increasing the overall saturation area within the free space mixing chamber.

The lower reservoir tank part (31) comprises at the top lip an outward flange (80) where upon the upper lid part sits and allows for the engagement of the micro-switch. The outward flange also produces a friction means by increasing overall contact area to prevent the turning of the upper lid part by torque during operation. At the underside of said reservoir tank are sticky pads (81) that allow the apparatus to sit on a table or countertop without movement during operation, and without damage to said furniture.

Said apparatus includes a standard home appliance electric cord, an inline on/off switch and GFCI protected plug for enhanced safety means. This invention may take any desired shape or form (i.e. round, square, tall, short) as may be desired to accommodate particular operational conditions.

The invention seeks to expose air to an aromatic substance, the method embodied as an apparatus having a housing comprising an upper lid part (30) and a lower reservoir tank part (31), wherein air is inducted (21*b*) into the apparatus through at least one air inlet hole (21*a*) in said lid. Induction of air into the apparatus occurs as a function of a motor (32) rotating an impeller (36) generating a vacuum within an air intake housing (35) chamber. Inducted air flows downwardly out through the ribs of said rotating impeller (22) and into the free space mixing chamber (25*a*). Air inside said free space mixing chamber comes into direct contact with spraying aromatic liquid substance (24) discharged in a 360 degree fashion from the outlet channels of the rotating impeller assembly. The aromatic liquid substance is pumped up to the outlet channels of said impeller assembly by a rotating (20) draw tube (37) the smallest end (23) of which is deeply submersed within the aromatic liquid substance (26), while at the same time generating an ongoing mixing of said aromatic liquid substance resting in said reservoir tank by applied kinetic energy from said rotating draw tube. Air inside said free space mixing chamber takes on elements of the aromatic liquid substance while at the same time moving upwardly toward at least one air outlet hole (25*b*) located in said upper lid part, wherein said air is discharged back into the environment as aromatized air. This method of exposing air to an aromatic substance is free from the specific application of gas, fire, heat, or a directly applied electric source. This invention uniformly exposes air to an aromatic substance, and said aroma laden air is then discharged in a uniform manner.

This invention is a viable alternative, as well as a practical and safe apparatus and method, for exposing air to an aromatic substance.

What is claimed is:

1. A device for exposing air to an aromatic substance, said device comprising:

a housing having an upper part and a lower part, the upper part being embodied as a lid that includes air inlet means and air outlet means;

a motor disposed under the lid and protected by a motor cover, having an output shaft situated axially, and a motor activation means controlled by depression of a micro-switch;

an impeller means for inducting air into the device through an air inlet hole(s) in the lid, through an attached air intake housing structure providing air-flow guidance means, said impeller also providing a means for pushing the inducted air through hollow free space in the device housing toward an outlet hole(s) in the lid;

a conically shaped hollow draw tube disposed onto an underside of the impeller for fluid pumping means, is situated axially and rotates cooperatively with impeller, the apposing end comprising a small hole which is immersed in a liquid solution, a means for a 360 degree radial discharge of said fluid through wide and narrow outlet channels located upwardly and axially of the draw tube as draw tube is rotated; and a lower base part being embodied as a reservoir tank that serves for holding an aromatic liquid solution, with a remaining free space to be formed in the tank above the surface of the liquid therein allowing an air flow means through the device housing, providing a mixing chamber area; an outward pointing flange comprising the lip of the reservoir tank providing a micro-switch engagement means.

2. A device for exposing air to an aromatic substance as claimed in claim 1, further comprising: said pump means via a draw tube having an axis of rotation and taking the form of a conical tube that tapers downward toward the direction of said reservoir tank and has a liquid inlet opening disposed just above said reservoir tank base and well below liquid level, and internally comprising ribs extending downward and axially providing enhanced pumping stability means and fluid flow rate means;

an interlocking mechanism providing for a means to securely attach draw tube to the underside of impeller;

a series of small outlet channels formed when draw tube is attached to underside of impeller, located upwardly and axially of the draw tube, providing a means to distribute liquid laterally and downwards when the draw tube is rotated at expected rpm, wide and narrow outlet channels cooperating to reduce droplet size during distribution, thus improving distribution area of liquid droplets, and thereby maximizing potential for said aromatic liquid to come into contact with air flowing through said device housing.

3. A device for exposing air to an aromatic substance as claimed in claim 1, further comprising:

said motor cover providing a means to shield motor with respect to splashing liquid and a blowing path;

a neoprene washer sitting tightly between the motor face and the motor housing, and around the output shaft, providing additional means to shield motor with respect to splashing liquid and the blowing path.

4. A device for exposing air to an aromatic substance as claimed in claim 1, further comprising: said air intake housing structure guiding air inducted through air inlet hole(s), and providing a means to forcibly move air into contact with spraying liquid in the free space mixing chamber, and ensuring enough guided force to move mixed air upwards and out of the device through the air outlet hole(s).

5. A device for exposing air to an aromatic substance as claimed in claim 1, further comprising: said micro-switch coming into contact with the outward pointing flange comprising the edge of the reservoir tank, activating the motor; when said lid is lifted slightly from reservoir tank, said micro switch disengages the motor providing a safety means from moving parts when upper and lower housing parts are separated.

6. A device for exposing air to an aromatic substance as claimed in claim 1, further comprising: said reservoir tank is provided with a liquid level guideline providing a means of knowing when the liquid level is correct too low, or too high for proper operation.

7. A device for exposing air to an aromatic substance as claimed in claim 1, further comprising: said device housing has smooth inner surfaces to facilitate effortless cleaning.

8. A device for exposing air to an aromatic substance as claimed in claim 1, further comprising: said lid underside has a vertical ridge extending around the circumference of the lid, wrapping closely around the lip of the reservoir tank thus providing a means to tightly seal the internal operations of the device, and to prevent the leaking of fluids during operation.

9. A device for exposing air to an aromatic substance as claimed in claim 1, further comprising: said underside of lid comprises horizontal ribs around the very outer circumference of the lid providing a means for the lid to sit evenly atop the lip of the reservoir tank, also providing a friction means to prevent lid from twisting from operational torque.

10. A device for exposing air to an aromatic substance as claimed in claim 1, further comprising: said reservoir tank has applied small sticky pads on the underside to provide a means of preventing movement of the device during operation; preventing harm to a table surface.

11. A device for exposing air to an aromatic substance as claimed in claim 1, further comprising: said lid has a ventilation outlet on the top providing a means for convective ventilation of heat generated by the motor.

12. A device for exposing air to an aromatic substance as claimed in claim 1, further comprising: said device may be comprised of an AC motor or a DC motor.

* * * * *